United States Patent [19]

Hunt et al.

[11] Patent Number: 4,999,498
[45] Date of Patent: * Mar. 12, 1991

[54] REMOTE SENSING GAS ANALYZER

[75] Inventors: Robert N. Hunt, Wheeling; Robert L. Sandridge, Proctor, both of W. Va.

[73] Assignee: Mobay Corporation, Pittsburgh, Pa.

[*] Notice: The portion of the term of this patent subsequent to Jan. 3, 2006 has been disclaimed.

[21] Appl. No.: 361,169

[22] Filed: Jun. 5, 1989

[51] Int. Cl.$^5$ .............................. G01J 3/45; G01J 3/00
[52] U.S. Cl. ............................... 250/338.5; 250/338.1; 250/339; 250/347
[58] Field of Search .................... 250/338.1, 338.5, 339, 250/347, 352

[56] References Cited

U.S. PATENT DOCUMENTS

| | | | |
|---|---|---|---|
| 3,766,380 | 10/1973 | Menzies | 250/343 |
| 3,925,666 | 12/1975 | Allan et al. | 250/338 |
| 4,319,843 | 3/1982 | Gornall | 356/346 |
| 4,490,043 | 12/1984 | Cramp | 356/407 |
| 4,520,265 | 5/1985 | Griggs et al. | 250/338.5 |
| 4,529,317 | 7/1985 | Cramp | 356/407 |
| 4,795,253 | 1/1989 | Sandridge et al. | 356/51 |
| 4,799,001 | 1/1989 | Burch | 318/640 |

OTHER PUBLICATIONS

William F. Herget, Remote and Cross-Stack Measurement of Stack Gas Concentrations Using a Mobile FT-IR System, Applied Optics, vol. 21, No. 4, Feb. 1982, 635-641.
William F. Hertet et al, Remote Fourier Transform Inrrared Air Pollution Studies, Optical Engineering, vol. 19, No. 4, Jul./Aug. 1980, 508-415.

Primary Examiner—Constantine Hannaher
Assistant Examiner—Edward J. Glick
Attorney, Agent, or Firm—Joseph C. Gil; Lyndanne M. Whalen

[57] ABSTRACT

A particular area or areas are monitored for the presence of gaseous materials, particularly pollutants by analyzing background infrared radiation present in the selected area with a spectrometer and making the results of this analysis available in a form understandable to the person or device monitoring the area for the presence of specified gaseous materials. The results of the spectrometric analysis may, for example, be displayed on a video unit or they may be printed. Apparatus useful in the practice of this invention generally includes an interferometer of the Michaelson-Morely type having specific optical characteristics, a sensitive infrared detector, electronic data processor, and a device which records and/or displays the results of the determination(s).

In a preferred embodiment, no radiation concentrating or focusing elements are used ahead of the beamsplitter of the Michelson-Morely interferometer, said interferometer having imaging optics which, combined with detector size, results in the optical field of view being essentially no larger than the area of the remote source employed.

13 Claims, 1 Drawing Sheet

REMOTE SENSING GAS ANALYZER

BACKGROUND OF THE INVENTION

The present invention relates to a method for monitoring a boundary or fenceline for gaseous materials present in the atmosphere of a selected area and to apparatus useful therefor.

In production facilities, particularly chemical production facilities, potentially hazardous materials are often employed. To reduce the risk of production, handling and use of such materials, detection of the presence of their vapors in the atmosphere before dangerous levels are reached is desirable. Continuous monitoring of the atmosphere of the production or handling facilities is one way to ensure early detection of undesirable materials in the atmosphere.

Many approaches for monitoring the atmosphere for the presence of pollutants have been explored. U.S. Pat. No. 3,766,380 and U.S. Pat. No. 3,925,666, for example, disclose methods in which an infrared laser beam is transmitted through the atmosphere. The reflections of this transmitted laser beam are collected and analyzed for information relating to the presence of gaseous pollutants. In each of these disclosed methods, the wavelength of the transmitted laser beam must be chosen to detect a specific gaseous pollutant. Consequently, a second different pollutant could be detected on the same device and discriminated from the first pollutant only if a laser beam having a wavelength different from that used to detect the first pollutant were used. It would not therefore be possible to continuously monitor the atmosphere for several hazardous materials with a single device by the process disclosed in these two patents. In fact, continuous monitoring for more than one pollutant would be possible only by using as many devices as there are gaseous pollutants possible in the monitored area.

U.S. Pat. Nos. 4,490,043 and 4,529,317 each disclose a method for monitoring gaseous pollutants in which multiple transmitted laser beams are employed. In U.S. Pat. No. 4,490,043, two laser beams at different frequencies are employed. One beam has a wavelength specific to the gas or gases being monitored and the other beam is a reference beam at a nearby wavelength which does not have absorption bands from the pollutant or other compounds. This method is limited to detection of a specific pollutant or pollutants whose presence in the environment is expected. Further, this method requires variation of the amount of radiation reaching the detector in order to prevent overload to the detector when the beam scans areas of high reflectivity, thus limiting the quantitative capabilities of the device. Furthermore, this method gives only the direction of the gas and not the distance of a gas cloud or concentration of the gaseous material.

In the monitoring method disclosed in U.S. Pat. No. 4,529,317, at least two scanning beams, each containing multi-plexed reference and measuring wavelengths are directed towards the location to be monitored from two spaced-apart scanning positions. Combination of information from the two signals provides a measure of the amount of gas at the intersection of the two beams. As in the method disclosed in U.S. Pat. No. 4,490,043, the reference beam wavelength is selected on the basis of the particular pollutant expected to be present in the environment. Continuous monitoring for the presence of more than one pollutant can not therefore be accomplished with a single device.

In each of the above-described systems and any other infrared laser-based systems, only a limited number of discrete wavelengths can be generated by the laser and used for measuring and reference beams. The available wavelengths may not however be well matched to the absorption peaks of interest. Consequently, lower sensitivity of the system and increased likelihood of interference from other pollutants results. In addition, since only one measuring wavelength is normally considered, any other compound which absorbs at the selected frequency would give a signal which would be indistinguishable from the signals given by the pollutant of interest. Interference in the measurement of the pollutant being monitored would result.

The Environmental Protection Agency has pursued methods for monitoring the atmosphere for gaseous pollutants which would not be limited to detection of only one compound at a time. A brief history of The Environmental Protection Agency's attempts to use remote optical sensing of emissions (ROSE) systems in which commercial Fourier Transform infrared spectrophotometers are used is given by Herget et al in "Remote Fourier Transform Infrared Air Pollution Studies," *Optical Engineering*, Volume 19, No. 4, pages 508–514 (July/August 1980). Herget et al also describes an improved mobile ROSE system in this article. Actual tests conducted with this improved mobile system are described in Herget's "Remote and Cross-stack Measurement of Stack Gas Concentrations Using a Mobile FT-IR System" in *Applied Optics*, Vol. 21, No. 4, pages 635–641 (Feb. 15, 1982).

One of the EPA's first ROSE systems was a mobile system designed to detect and measure pollutants present at various pollution sources from a point remote from the pollution source. In this system, interferograms collected in the field were returned to a central computer for processing. This delay between data collection and data processing was undesirable because it made it difficult, if not impossible, to detect a leak before it had spread and created a potentially hazardous condition. This early system was subsequently improved to permit on-site processing.

Herget et al reports that these ROSE systems were subsequently further modified to include an interferometer system capable of detecting wavelengths in the infrared spectral region of from 650 to 6000 cm$^{-1}$. This ROSE system could be transported in a van-sized vehicle to a location near the area to be monitored. In this most recent ROSE system, a light source and a source telescope are first positioned at a site remote from the site to be monitored. Energy from this remote light source is collected by a receiver telescope through an opening in the van wall. A tracking mirror reflects the infrared signal of gas(es) emitted from a stack of the facility being monitored into the receiving telescope. The receiving telescope focuses energy from the remote light source and the infrared signal of the gas(es) at the interferometer aperture. The interferometer detector which has a dual element sandwich-type configuration mounted in a liquid nitrogen Dewar scans two infrared regions (i.e. 1800 to 6000 cm$^{-1}$ and 600 to 1800 cm$^{-1}$) separately. Selection of the desired detector element is made by command (via computer). Two beamsplitters are employed in the interferometer. A beamsplitter interchange and realignment takes about five minutes.

Pollutants which do not exhibit characteristic infrared peaks in the range of the selected beamsplitter (i.e. either 650-1800 cm$^{-1}$ or 1800 to 6000 cm$^{-1}$) can not be identified without a beamsplitter interchange and realignment. Such interchange and realignment, however, take about five minutes. Consequently, if two pollutants were present in a monitored area simultaneously and one of those pollutants had a characteristic IR band at 1700 cm$^{-1}$ and the other had a characteristic band at 1900 cm$-1$, the ROSE system could not detect and monitor both pollutants simultaneously.

Yet another disadvantage of the ROSE system is the initial set up time of two to three hours. The length of time required for set up makes the ROSE system almost useless for detecting a leak in its early stages unless the system is permanently installed at the location of the leak or a leak happens to occur during the scheduled monitoring of an area.

Finally, the primary mirrors of the ROSE System are not suitable for continuous exposure to corrosive industrial atmospheres.

Another improved system for monitoring gaseous pollutants is presently being marketed by Bomem Corporation. Detailed information with respect to the construction and operation of this Bomem system are not yet available to Applicants. However, it is apparent from advertising literature for this system that the optical components used in this system and the design of the instrument would not withstand the corrosive atmospheres encountered in many industrial environments.

The U.S. Army has also announced that it is working on a tripod mounted sensor device capable of detecting chemical vapors at distances of up to five kilometers. Specific details about the structure of this device have not, however, been released.

U.S. Pat. No. 4,795,253 discloses a remote gas analyzer capable of monitoring an area for the presence of gaseous material in which background radiation is collected by large mirrors, analyzed with a spectrometer and the results of the analysis are displayed or recorded.

SUMMARY OF THE INVENTION

It is an object of the present invention to provide a method and apparatus for continuously monitoring an area for the purpose of detecting one or more gaseous materials in the atmosphere of that area.

It is also an object of the present invention to provide a method and apparatus for continuously monitoring the atmosphere of a selected area for the presence of any gaseous materials particularly hazardous vapors having suitable absorption or emission peaks in the infrared region.

It is a further object of the present invention to provide a method for monitoring a boundary or fenceline of a facility for the presence of gaseous contaminants in the atmosphere.

It is yet another object of the present invention to provide a lightweight, relatively portable apparatus capable of detecting the amount of any infrared absorbing or emitting gaseous material in the atmosphere of a selected area and of displaying the results in a manner understandable to a monitor or human observer.

It is a further object of the present invention to provide a method and apparatus capable of detecting the amount and/or presence of any infrared absorbing or emitting material in the atmosphere of a selected area, analyzing a significant portion of the infrared spectrum of the radiation coming from the area, and if desired, providing a permanent record of the results, either as a computer file or as a plotter-generated infrared spectrum.

It is another object of the present invention to provide a method and apparatus capable of detecting the location and limits of a gas cloud of any infrared absorbing or emitting material in a selected area and displaying such information in a form understandable to a monitor or human observer.

It is also an object of the present invention to provide an apparatus capable of detecting the amount and/or presence of any infrared absorbing or emitting material in the atmosphere in which the design and construction of the device is particularly suitable for continuous, automatic, low maintenance, unattended monitoring of industrial fencelines and boundaries over extended periods of time.

These and other objects which will be apparent to those skilled in the art are accomplished by analyzing background infrared radiation (and optionally visible radiation) present in the selected area with a suitable spectrometer such as an FTIR spectrometer and making the results of this analysis available in a form understandable to the person or device monitoring the area for the presence of specified gaseous materials. The results of the spectrometric analysis may, for example, be displayed on a video unit or they may be printed, or they may be used to activate a suitable alarm system.

Apparatus useful in the practice of this invention must include (a) an opening which is preferably covered with an infrared window through which infrared radiation and preferably also visible radiation will pass, (b) an interferometer capable of analyzing infrared radiation within a predetermined range of wavelengths and having optical components and detector particularly suited to the needs of long range remote monitoring, and (c) means for communicating the results of the interferometer analysis being monitored to a monitoring device, an observer or recording device. Such apparatus generally includes (a) a containing vessel having (1) an infrared window through which remote infrared radiation will pass, (2) optics suitable for directing the collected energy into a spectrometer, (3) an interferometer of the Michaelson-Morely type and (4) a cooled high-sensitivity infrared detector, and (b) means for data reduction and data storage such as a computer. A video camera for viewing the scene being monitored may also be employed.

DETAILED DESCRIPTION OF THE INVENTION

Figure 1:
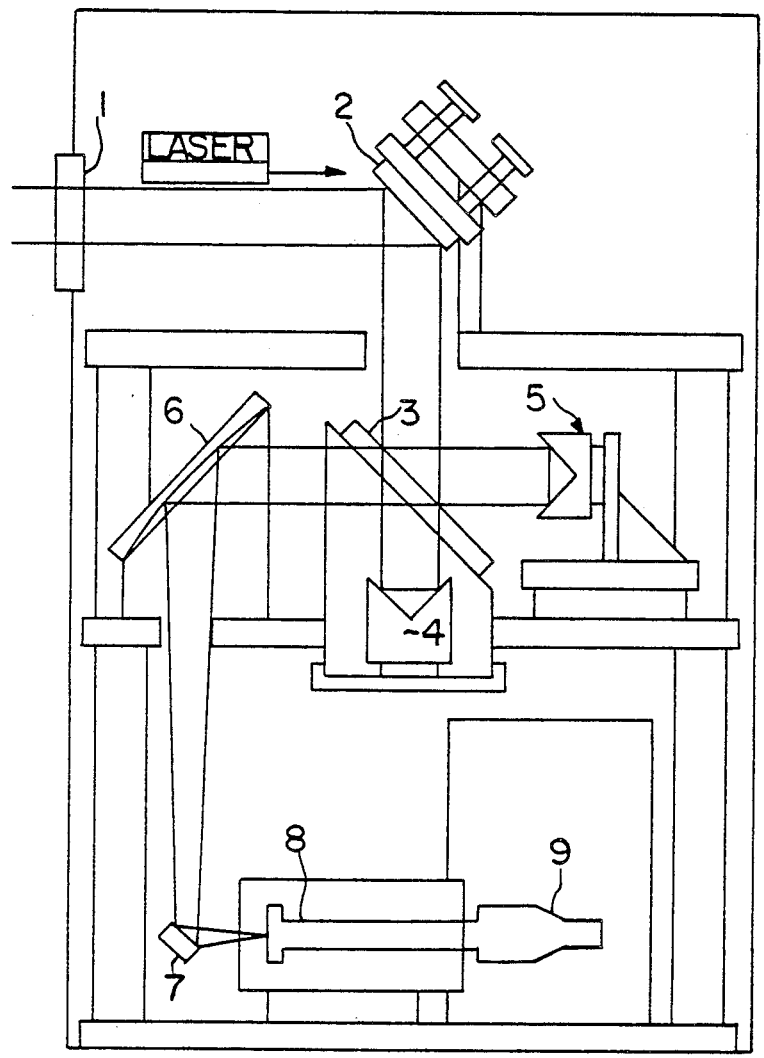
FIG. 1 is a schematic representation of one embodiment of the inventive apparatus in which the infrared radiation to which the apparatus is exposed is analyzed.

The present invention relates to a method for detecting the presence and/or quantity of an infrared absorbing or emitting gaseous material present in the atmosphere of the location of the apparatus and to apparatus useful in such detection.

Background radiation is emitted by any object which is at a temperature above absolute zero. A gas present between such an object and a detection device may produce either an emission or an absorption spectrum depending upon the temperature of that gas in relation to the background object or objects. Specifically, if the background object is at a temperature lower than that of the gas, the gas will produce an emission spectrum. Conversely, if the background object is at a temperature higher than that of the gas, the gas will produce an absorption spectrum. If, however, the background object is at the exact same temperature as the gas to be detected, no spectrum is obtainable. The likelihood that the temperature of a background object and the temperature of a gas present in the atmosphere will not differ by at least several tenths of a degree is however extremely remote. A spectrum may therefore be obtained in virtually any environment at a temperature greater than absolute zero.

In areas such as industrial plants, remote infrared sources are generally installed to provide strong, reproducible infrared emitting backgrounds against which the absorption patterns of gases may be readily measured.

In principle, it is possible to determine the relative concentration of a particular material in a specific area from the emission or absorption spectrum generated by that material. The precision of such determination is however dependent upon factors such as the particular apparatus employed, the temperature difference between the background object(s) and the particular gaseous material(s), the distance between the area being monitored and the spectrometer, the weather, etc. Under optimum conditions, however, the apparatus of the present invention is capable of detecting a gas at a level as low as 1 part per million per meter.

One embodiment of an apparatus within the scope of the present invention is illustrated in FIG. 1. In the device shown in FIG. 1, infrared radiation and optionally, visible radiation present in the area in which the monitoring device is located are allowed to pass through infrared window 1 located in a containing vessel. The containing vessel may be made of any material capable of withstanding the environment in which the apparatus is to be placed. Window 1 is transparent to both visible and infrared radiation. The window 1 used in this apparatus was a clear polyethylene film having a diameter of 5 cm. Window 1 need not have any specific diameter but it is preferred that it have a diameter which is at least as large as that of beamsteering reflector 2 and preferably larger than that of reflector 2. A polyethylene window is preferred and was selected because it is transparent in the visible region and has bands in the infrared region which do not interfere with the purpose of the instrument. However, any material which is capable of passing visible light and infrared light in the required regions without a substantial degree of distortion (e.g., optical grade zinc selenide plates) may be employed.

Reflector 2 is a permanently mounted flat reflective surface such as a mirror which is positioned to receive and reflect substantially all of the infrared radiation which passes through infrared window 1. Reflector 2 may be a mirror having a diameter which is at least large enough to reflect substantially all of the infrared radiation passing through window 1 to beamsplitter 3. A mirror having a a protected aluminum surface and a diameter of 7.5 cm was used in the apparatus illustrated in FIG. 1 but any of a number of known reflective coating materials may be used to coat the surface of reflector 2, provided the coating is sufficiently durable and corrosion resistant. Any material which reflects infrared and optionally visible radiation very well and which is resistant to tarnish and oxidation is suitable for reflector 2. The reflector should be coated in a manner such that it will have a high degree of surface accuracy. That is, the surface should reflect a ray in a manner such that the reflected ray does not deviate substantially from its ideal path.

In the device shown in FIG. 1, the infrared and visible radiation reflected by reflector 2 are passed through a beamsplitter 3. This beamsplitter 3 may be made of any material capable of separating collected infrared radiation into at least two beams. In a preferred embodiment, beamsplitter 3 is a disc made of zinc selenide. Beamsplitter 3 has a diameter which is at least large enough to receive substantially all of the radiation reflected by reflector 2. In the device illustrated in FIG. 1, beamsplitter 3 has a diameter of 7.5 cm. A portion of the infrared radiation passes through beamsplitter 3 onto the surface of a fixed retroreflector 4 (e.g., corner cube mirror) which further reflects that radiation via beamsplitter 3 to the surface of an off axis parabolic mirror 6. A portion of the collected infrared radiation is also directed by beamsplitter 3 onto the surface of a moving retroreflector 5 (e.g., corner cube mirror) which further reflects that radiation through beamsplitter 3 and onto off axis parabolic mirror 6. The beams generated by beamsplitter 3 and retroreflectors 4 and 5 are reflected onto off axis parabolic mirror 6 which focuses the combined beams onto infrared detector 8 via beam steering reflector 7. Infrared detector 8 is preferably cooled to improve sensitivity and to improve signal to noise ratio by any system capable of maintaining the detector at a temperature below ambient temperature. The interferogram signal from detector 8 is transmitted to the signal processor (converter) 9. A preamplifier such as a low noise electronic amplifier to adjust the interferogram signal to match the dynamic range of the analog-to-digital converter 9 may optionally be included. Converter 9 digitizes the interferogram sent to a computer (not shown) for analysis.

Infrared window 1 is used in this apparatus to protect the reflective surfaces and detector but such a window is not required. It would theoretically be possible to omit this protective window as long as an opening through which infrared radiation could pass was present. It is not, however, recommended that such protective window be omitted in view of the environments in which the gas sensor will be used. As was briefly discussed above, the window may be made of a material such as a clear polyethylene film. The window need not have any specific diameter, but should not obstruct the field of view of the apparatus. A polyethylene window is preferred because it is transparent in the visible region and has bands in the infrared region which do not interfere with the purpose of the instrument. However, any material which is capable of passing infrared radiation light in the required regions without a substantial degree of distortion (for example, optical grade zinc selenide plates) may be employed. No specific distance between window 1 and reflector 2 is required.

Reflector 2 is a fixed flat front surfaced mirror which is readily adjusted to direct energy from an area to the beamsplitter. It can be positioned at any angle which allows radiation coming from a selected area to be directed to the beamsplitter. In one embodiment of the present invention, reflector 2 may be eliminated and the body of the apparatus positioned so that radiation coming from the area to be monitored falls directly on beamsplitter 3.

The beamsplitter 3 used in this apparatus was a zinc selenide beamsplitter having a diameter of 7.5 cm. However, any of the known commercially available beamsplitters having an appropriate diameter and the ability to split infrared radiation may be used. In FIG. 1, a flat plate beamsplitter arranged at an angle of 45° from the axis of the incoming optical beam was used. Any angle which allows separation of reflected radiation from the front and back surface of the beamsplitter could, however, be used advantageously.

A portion of the beam of infrared radiation is reflected by beamsplitter 3 to retroreflector 5 which is a corner cube retroreflector. Retroreflector 5 reflects that beam back through the beamsplitter 3 to the off-axis parabolic reflector 6. Simultaneously, a second portion of the infrared beam is transmitted through beamsplitter 3 to retroreflector 4 (also a corner cube retroreflector) which reflects that beam back to the beamsplitter 3 which reflects it to the off-axis parabolic reflector 6. Each of the retroreflectors 4 and 5 is a hollow-corner cube construction of three coated optical flat plates assembled into a mutually orthogonal corner. The retroreflectors used in the device shown in FIG. 1 have a gold coating with a silicon oxide protective overcoat, an aperture of 2.0 inches and a 0.5 arc second accuracy. However, reflectors with any other coating (e.g., aluminum) which will permit reflection of the infrared radiation without substantial distortion or reflection loss would be suitable. Corner cube retroreflectors are preferred because of the ease with which they may be properly aligned. However, in principle, any reflective surface which would reflect infrared radiation without substantial distortion could be used as retroreflector 4 and/or 5. Because reflective surfaces such as flat plate mirrors are difficult to align properly and improper alignment results in a poor interferogram, corner cube retroreflectors are preferred.

In FIG. 1, the retroreflector 5 is mounted on a motor driven moveable stage for generation of the interferogram. The stage could however be used as the mount for either retroreflector 4 or 5. A constant speed motor and gear train is used to drive the circular cam (not shown) for the mirror stage at about 20 rpm. A cam moves the precision roller-bearing stage back and forth in a smooth reciprocating motion through about 1 inch of travel. This arrangement was selected to provide a rugged, trouble-free mechanism for generating the interferogram. Other systems such as constant-velocity, voice-coil driven air bearing stages, may be used but they do not provide equivalent mechanical durability. The distance of travel of the moveable stage may be varied, but that distance must be long enough to obtain the desired degree of spectral resolution. In the instrument shown in FIG. 1, one inch of travel in the moveable stage provided better than 1 cm$^{-1}$ of spectral resolution. The period of reciprocation and distance of stage travel are selected to match the characteristics of the active electronic filters in the signal processor 9. This arrangement allows a high signal-to-noise ratio to be achieved without time-averaging several interferograms or spectra. High resolution spectra may therefore be obtained in a minimum amount of time. For example, spectra can be obtained in less than 3 seconds under typical operating conditions. For simplicity and durability, it is preferred to operate the mirror stage with a fixed period and distance of travel. However, other systems which vary the velocity and travel under controlled conditions may also be used very effectively.

The object of having a moving mirror 4 or 5 is to vary the optical path length between the beamsplitter and the moving mirror relative to the path length between the beamsplitter and the fixed mirror. The interferogram is created upon recombination of the beams. Other means of varying the pathlength of one beam relative to the other may however be employed. For example, a moving refractive wedge may be used in combination with two fixed mirrors. The optical path length could also be varied by moving two mirrors in relation to the beamsplitter.

A means for precisely determining the position of movable retroreflector 5 (not shown in FIG. 1) should be employed to trigger data collection. One such means which has been found to be particularly advantageous is a 0.5 milliwatt HeNe laser. This laser is positioned so that its beam is in the optical path of the interferometer (defined at page 16). The laser beam is directed onto a PIN diode detector (also not shown). Interference fringe counting techniques are applied to the output of the diode detector to determine the position of retroreflector 5.

The recombined infrared beam generated by beamsplitter 3 is reflected and focused by the off-axis parabolic reflector 6 to the infrared detector 8 via reflector 7.

Off-axis parabolic reflector 6 is a commercially available diamond turned mirror with a bright rhodium coating having a focal length of 25 cm and a clear aperture of 3 inches (7.62 cm). In order to achieve the desired precision with the apparatus of the present invention, the ratio of the focal length of reflector 6 to clear aperture of reflector 6 should generally range from about 1 to about 32. Any other off-axis parabolic reflectors such as those cut from a large parabolic mirror are also suitable if they have the required relationship between focal length and clear aperture. An infrared transmitting lens could also be substituted for the off-axis parabolic reflector 6 if the ratio of focal length to clear aperture is within the range of from about 1 to about 32.

Reflector 7 is a flat front-surfaced mirror in the apparatus illustrated in FIG. 1. Any reflective surface capable of receiving the beam from Reflector 6 and of reflecting that beam without substantial distortion to infrared detector 8 may, however, be used.

Any commercially available infrared detector having suitable sensitivity and frequency response and an active sensor area in the range of from about 0.0001 to about 4 square millimeters may be used in the apparatus of the present invention. In the apparatus illustrated in FIG. 1, a high quality HgCdTe infrared detector having an active area of 0.01 mm$^2$ mounted in a Dewar with a miniature cryostat was used. The cryostat and Dewar were fixed in an aluminum housing with cable for signal output. A silicon diode temperature sensor monitors the cryostat performance. The cryostat is cooled by a single stage closed cycle helium compressor. Temperatures lower than ambient temperatures are preferred because the sensitivity of the detector is greater at cooler temperatures (e.g. 75°–80° K.). Any other suitable cooling device or technique may be used in accordance with the present invention.

The detector 8 used in the apparatus illustrated in FIG. 1 was a photoconductive HgCdTe detector capable of detecting infrared radiation in the 8–14 μm range which range would include at least one characteristic identifying band for substantially all of the gaseous pollutants expected to be found in the monitored area. However, any of the commercially available detectors of the required size with the capability of detecting infrared radiation within a desired range could be used. The preferred infrared range of a particular detector will of course be dependent upon the specific environment being monitored. Detectors capable of detecting infrared radiation in virtually any selected region are commercially available.

The interferogram signal from detector 8 may optionally be transmitted to an infrared detector preamplifier (not shown). A low noise electronic amplifier may be used to match the dynamic range of analog-to-digital converter 9 to the detector 8. Active electronic filters are used to reject unwanted frequencies coming from the interferometer and thereby significantly improve the signal-to-noise ratio of the final spectrum. The analog-to-digital converter digitizes the interferogram to be sent to a data reduction device (not contained in the containing vessel) such as a computer(not shown).

Although a computer was used in the apparatus of FIG. 1, any device capable of reducing the data received from the infrared detector may be used. Possible alternatives to a computer include optical processors and digital processors.

The computer which was used in the apparatus shown in FIG. 1 had been programmed for fast Fourier Transform of the collected data but any program which is capable of reducing the collected data to a useful form could be employed. The computer may also be programmed to compare the wavelength of the detected infrared radiation with reference wavelengths of the gases expected to be present in the atmosphere being monitored. However, such comparative programming is not essential to the present invention.

The preferred operating parameters for the gas sensors of the present invention are as follows. The focal length of off-axis reflector 6 should be in the range of from about 1 to about 200 cm. The diameter of window 1 should be no greater than 25 cm. The area of the aperture of detector 8 should range from 0.0001 to 4 square millimeters. The field of view of the apparatus $$\left(\text{i.e., } \frac{\sqrt{\text{detector area, cm}^2}}{\text{focal length of reflector 6, cm}}\right)$$

should be from 0.2 to 10 milliradians. The f stop of the device (i.e., the ratio of focal length of off-axis reflector 6 to the clear aperture of reflector 6) should be from about 1 to about 32.

A key feature of the apparatus of the present invention is the absence of a radiation concentrating or focusing element positioned before the interferometer. The ability to use relatively small optical components in the apparatus of the present invention without sacrifice of measurement capability is also advantageous because the gas sensor can be made small enough to be mounted without heavy structural supports.

The apparatus of the present invention makes it possible to scan along a plant fenceline on a continuous basis until a leak is detected. Use of several devices positioned at strategic locations throughout the plant makes it possible to monitor all sides of a plant unit for gas leaks. Such information is essential if measures necessary to neutralize that leak are to be taken before the leak becomes a hazard to plant workers and surrounding communities.

If more than one detector device is employed to monitor a large area e.g., an entire plant, the data from each infrared detector may be transmitted to a central computer directly from the detector or from a smaller computer. Such centralization is particularly useful in cases in which the path of a gas cloud is to be followed.

It is also possible to incorporate an alarm system into the apparatus of the present invention which alarm system would be activated by a computer whenever a particular pollutant had been detected at a level exceeding a pre-programmed limit. Suitable alarm systems are known in the art and may be readily incorporated into the apparatus of the present invention.

The beamsplitter 3, retroreflectors 4 and 5, off axis parabolic mirror 6, reflector 7, infrared detector 8 and signal processor 9 are hereafter collectively referred to as the "interferometer". It is preferred that the components of the interferometer be mounted and arranged in a manner which makes them resistant to the effects of ambient temperature changes, vibrations and mechanical stresses.

The interferometer shown in FIG. 1 covers a continuous band of infrared wavelengths between 8 and 14 $\mu$m. However, the band of wavelengths covered by the interferometer may be varied by selection of a beamsplitter 3 and detector 8 having the capability of covering the desired range. Multiple wavelength bands within the capacity of the beamsplitter may be monitored simultaneously by using several detectors, each of which is useful within a range different from that of the others.

The present invention makes it possible to continuously monitor a predetermined area for the presence of more than one gaseous material with a single interferometer. In fact, the number of gases present in the atmosphere which may be monitored at any given time is limited only by the capacity of the computer and the requirement that at least one identifiable peak of the compound be present within the spectral range of the instrument. Since virtually every composition which would be monitored by a system of the type of the present invention produces at least one characteristic peak or a combination of peaks within the 3–5 or the 8 to 14 $\mu$m wavelength range, the above-described monitoring apparatus is capable of detecting a wide variety of substances without the expensive narrow band interference filters for each gas to be detected required in many of the known monitoring systems.

The output of the infrared detector 8 is an interferogram which is processed preferably by a fast Fourier Transform Algorithm in a computer to produce an emission or absorption spectrum. In addition to the processing of the interferogram, the computer may analyze the spectrum for peaks corresponding to specified (pre-programmed) materials such as toxic gases, may correlate collected data, etc. The result of such analysis may then be printed in a variety of forms and/or projected onto a video display unit.

The invention is further illustrated but is not intended to be limited by the following examples.

EXAMPLES

Example 1

An apparatus was assembled from the following components in accordance with the arrangement shown in FIG. 1.

Infrared window 1: A polyethylene film having a thickness of 4 mils and a diameter of 6 cm.

Reflector 2: Flat front-surfaced mirror, 7.5×7.5 cm sold by Melles Griot under the designation OIMFG013.

Beamsplitter 3: ZnSe infrared beamsplitter having a 7.5 cm diameter and sold by Laser Power Optics Corp.

Reflectors 4 and 5: Protected aluminum surfaced retroreflectors having a 1½ inch (~3.4 cm) clear aperture which is accurate to ½ second of arc sold by Precision Lapping and Optics Co.

Reflector 6: An off-axis parabolic reflector having a 5 cm clear aperture, a 25 cm. focal length, a 90° off-axis angle sold by Aero Research Associates, Inc.

Reflector 7: Flat front-surfaced mirror and mount, model number 2505 sold by Daedal Corp.

Infrared Detector 8: A HgCdTe infrared detector mounted in a metal Dewar sold by EEG Judson Corp. under the designation J-15D12-CCC-5100U-15. The Dewar was cooled by a helium closed cycle cooler (not shown) sold by Carlisle Cyrotronics Corp.

Signal processor 9: Preamplifier and signal processor of custom design having a band pass of 3–9 kilohertz.

Analog to Digital Converter (not shown): 14 bit analog to digital converter sold by Analog Devices Co. under the designation HAS-1409KM.

Computer (not shown): An IBM-AT computer sold by IBM Corporation.

Approximately 0.1 gm of phosgene was released at an outdoor site of a toluene diisocyanate production facility in which the above-described apparatus was present. A remote infrared source was located approximately 100 meters from the apparatus of the present invention in line with the point of gas release. This apparatus detected the presence of the phosgene and displayed a spectrum of the 8–14 μm infrared region containing absorption peaks characteristic of phosgene in less than 4 seconds.

Example 2

The apparatus used in Example 1 was positioned at an outdoor site aimed in the general direction of plant operating units. No remote infrared source was employed for the test. Approximately 1 grams of dichlorodifluoromethane was released at a distance of 80 meters from the apparatus. The apparatus detected the presence of the chlorofluorocarbon and displayed a spectrum of the 8–14 μm infrared region containing three absorption peaks characteristic of dichlorodifluoromethane in less than 4 seconds.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An apparatus for monitoring the atmosphere of a selected area for the presence of gaseous materials comprising
   (1) a container having:
      (a) an opening through which infrared radiation may pass,
      (b) a beamsplitter through which the infrared radiation that has passed through opening (a) passes and is split into at least two beams,
      (c) at least two reflective surfaces positioned to receive radiation from the beamsplitter,
      (d) means for varying the pathlength of at least one of the beams generated by the beamsplitter,
      (e) an off-axis parabolic reflector positioned to receive each of the combined beams reflected by (c) which off-axis parabolic reflector is characterized by a ratio of its focal length to its clear aperture in the range of from about 1 to about 32, and
      (f) a cooled infrared detector positioned at the focal point of off-axis parbolic reflector (e) and
   (2) a processor capable of anaylzing the output of infrared detector (f).

2. The apparatus of claim 1 in which a flat mirror is positioned to receive infrared radiation passing through the opening of (a) and to reflect that radiation to beamsplitter (b).

3. The apparatus of claim 2 in which the reflective surfaces of (c) are corner cube retroreflectors.

4. The apparatus of claim 3 in which opening (a) is covered with a polyethylene film.

5. The apparatus of claim 4 having a field of view in the range of from about 0.2 to about 10 milliradians.

6. The apparatus of claim 4 in which detector (f) has an aperture area in the range of from about 0.0001 to 4 square millimeters.

7. An apparatus for monitoring the atmosphere of a selected area for the presence of gaseous materials comprising
   (1) a container having:
      (a) an opening which opening is covered with a polyethylene film,
      (b) a flat mirror positioned to receive the infrared radiation passing through opening (a) and to reflect that radiation,
      (c) a beamsplitter through which the radiation reflected by (b) passes and is split into at least two beams,
      (d) a moveable retroreflector positioned to receive at least one of the beams generated by beamsplitter (c) and to reflect that beam back through beamsplitter (c),
      (e) a second retroreflector which may be moveable positioned to receive at least one beam generated by beamsplitter (c) which beam is different from that received by retroreflector (d) and which reflects the beam received back through beamsplitter (c),
      (f) an off-axis parabolic reflector characterized by a ratio of focal length to clear aperture in the range of from about 1 to about 32 positioned to receive the beams reflected by retroreflectors (d) and (e) through beamsplitter (c) and to reflect the combination of these beams, and
      (g) a cooled infrared detector to which the combination of beams reflected by off-axis parabolic reflector (f) is directed and
   (2) a processor capable of analyzing the output of infrared detector (g).

8. The apparatus of claim 7 in which a laser is included to determine the position of retroreflector (d).

9. An apparatus for monitoring the atmosphere of a selected area for the presence of gaseous materials comprising
   (1) a container having:
      (a) an opening which opening is covered with a polyethylene film,
      (b) a flat mirror positioned to receive the infrared radiation passing through opening (a) and to reflect that radiation to a beamsplitter,
      (c) a beamsplitter through which the radiation reflected by (b) passes and is split into at least two beams, (d) a moveable retroreflector positioned to receive at least one of the beams generated by beamsplitter (c) and to reflect that beam back through beamsplitter (c), (e) a second retroreflector which may be moveable positioned to receive at least one beam generated by beamsplitter (c) which beam is different from the received by retroreflector (d) and which reflects the beam received back through beamsplitter (c), (f) an infrared transmitting lens characterized by a ratio of focal length to clear aperture in the range of from about 1 to about 32, which lens is positioned to receive the beams reflected by retroreflectors (d) and (e) through beamsplitter (c) and to transmit the combination of these beams to an infrared detector, and (g) a cooled infrared detector to receive the combination of beams transmitted by leans (f) and (2) a processor capable of analyzing the output of infrared detector (g).

10. The apparatus of claim 9 in which a laser is included to determine the position of retroreflector (d).

11. A process for monitoring an area for the presence of gaseous materials in which the apparatus of claim 1 is placed at a site within the area to be monitored and the device is activated.

12. A process for monitoring an area for the presence of gaseous materials in which the apparatus of claim 7 is placed at a site within the area to be monitored and the device is activated.

13. A process for monitoring an area for the presence of gaseous materials in which the apparatus of claim 9 is placed at a site within the area to be monitored and the device is activated.

* * * * *